(12) United States Patent
Hoshino et al.

(10) Patent No.: US 7,135,315 B2
(45) Date of Patent: Nov. 14, 2006

(54) ALDEHYDE DEHYDROGENASE GENE

(75) Inventors: Tatsuo Hoshino, Kamakura (JP); Taro Miyazaki, Fujisawa (JP); Teruhide Sugisawa, Riehen (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/528,675

(22) PCT Filed: Sep. 22, 2003

(86) PCT No.: PCT/EP03/10498

§ 371 (c)(1),
(2), (4) Date: Aug. 5, 2005

(87) PCT Pub. No.: WO2004/029235

PCT Pub. Date: Apr. 8, 2004

(65) Prior Publication Data

US 2006/0127994 A1    Jun. 15, 2006

(30) Foreign Application Priority Data

Sep. 27, 2002  (EP)  ............ 02021650

(51) Int. Cl.
C12P 7/40    (2006.01)
C12P 7/60    (2006.01)
C12N 9/04    (2006.01)
C12N 1/20    (2006.01)
C07H 21/04   (2006.01)

(52) U.S. Cl. ............ 435/138; 435/136; 435/140; 435/252.3; 435/254.2; 435/410; 435/320.1; 536/23.2

(58) Field of Classification Search ........ 435/190, 435/136, 138, 252.3, 254.2, 410, 320.1; 536/23.2
See application file for complete search history.

(56) References Cited

U.S. PATENT DOCUMENTS 5,437,989 A    8/1995 Asakura et al.

FOREIGN PATENT DOCUMENTS

| EP | 0 790 301 A2 | 8/1997 |
|---|---|---|
| JP | 2002-125689 | 5/2002 |
| WO | WO 89/06688 | 7/1989 |
| WO | WO 02/34919 | 5/2002 |

OTHER PUBLICATIONS

Miyazaki T. et al. Pyrroloquinoline Ouinone-Dependent Dehydrogenases from Ketogluconicum vulgare Catalyze the Direct Conversion of L-Sorbosone to L-Ascorbic Acid, Applied and Environmental Microbiology, 2006, 72, 1487-1495.*
Saito, Y. et al., "Direct Fermentation of 2-Keto-$_L$-Gulonic Acid in Recombinant Gluconobacter oxydans," *Biotechnology and BioEngineering.*, vol. 58, No. 2&3, pp. 309-315 (1998).
Saito, Y. et al., "Cloning of Genes Coding for $_L$-Sorbose and $_L$-Sorbosone Dehydrogenases from Gluconobacter oxydans and Microbial Production of 2-Keto-$_L$-Gulonate, a Precursor of $_L$-Ascorbic Acid, in a Recombinant G. oxydans Strain," *Applied and Environmental Microbiology*, vol. 63, pp. 454-460 (1997).
Hoshino, T. et al., "Isolation and Characterization of NAD(P)-Dependent $_L$-Sorbosone Dehydrogenase from Gluconobacter melanogenus UV10," *Agric. Biol. Chem.*, vol. 55, No. 3, pp. 665-670 (1991).
Asakura and Hoshino, "Isolation and Characterization of A New Quinoprotein Dehydrogenase, $_L$-Sorbose/$_L$-Sorbosone Dehydrgenase," *Biosci. Biotechnol. Biochem*, vol. 63, No. 1, pp. 46-53 (1999).
Hancock and Viola, "Biotechnological approaches for $_L$-ascorbic acid production," *Trends in Biotechnology*, vol. 20, No. 7 (2002).
Derwent Database English language abstract of JP 2002-125689 (document B4 above).

* cited by examiner

*Primary Examiner*—Tekchand Saidha
*Assistant Examiner*—Malgorzata A. Walicka
(74) *Attorney, Agent, or Firm*—Bryan Cave LLP

(57) ABSTRACT

The present invention relates to a novel DNA which encodes aldehyde dehydrogenase (SNDH), an expression vector containing the DNA and recombinant organisms containing said DNA. Furthermore, the present invention concerns a process for producing recombinant aldehyde dehydrogenase protein and a process for producing L-ascorbic acid (vitamin C) and/or 2-keto-L-gulonic acid (2-KGA) from L-sorbosone by using the recombinant aldehyde dehydrogenase protein or recombinant organisms containing the expression vector. Also provided is a process for the production of 2KGA with a microorganism in which the gene encoding said aldehyde dehydrogenase is disrupted.

14 Claims, 5 Drawing Sheets

ALDEHYDE DEHYDROGENASE GENE

This application is the National Stage of International Application No. PCT/EP2003/010498, filed Sep. 22, 2003.

The present invention relates to a novel DNA which encodes aldehyde dehydrogenase (SNDH) derived from *Gluconobacter oxydans* DSM 4025, an expression vector containing the DNA and a recombinant microorganism containing the expression vector. Furthermore, the present invention concerns a process for producing recombinant aldehyde dehydrogenase protein and a process for producing L-ascorbic acid (vitamin C) and/or 2-keto-L-gulonic acid (2-KGA) from L-sorbosone by using the recombinant aldehyde dehydrogenase protein or the recombinant microorganism containing said expression vector.

Vitamin C is one of indispensable nutrient factors for human beings and has been commercially synthesized by the Reichstein process for about 60 years. Synthetic vitamin C is also used in animal feed even though farm animals can synthesize it in their own body. Although the Reichstein process has many advantageous points for industrial vitamin C production, it still has undesirable problems such as high energy consumption and usage of considerable quantities of organic and inorganic solvents. Therefore, over the past decades, many approaches to manufacture vitamin C using enzymatic conversions, which would be more economical as well as ecological, have been investigated.

The present invention is directed to an isolated nucleic acid molecule encoding aldehyde dehydrogenase which comprises a polynucleotide being at least 95% identical to the nucleotide sequence of SEQ ID NO: 1.

As used herein, "SNDH" stands for aldehyde dehydrogenase.

As used herein, "nucleic acid molecule" includes both DNA and RNA and, unless otherwise specified, includes both double-stranded, single-stranded nucleic acid, and nucleosides thereof. Also included are hybrids such as DNA-RNA hybrids, DNA-RNA-protein hybrids, RNA-protein hybrids, and DNA-protein hybrids.

As used herein, "mutation" refers to a single base pair change, insertion or deletion in the nucleotide sequence of interest.

As used herein, "mutagenesis" refers to a process whereby a mutation is generated in the DNA. With "random" mutagenesis, the exact site of mutation is not predictable, occurring anywhere in the chromosome of the microorganism, and the mutation is brought about as a result of physical damage caused by agents such as radiation or chemical treatment.

As used herein, "promoter" means a DNA sequence generally described as the 5' region of a gene, located proximal to the start codon. The transcription of the adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

As used herein, "percent identical" refers to the percent of the nucleotides or amino acids of the subject nucleotide or amino acid sequence that have been matched to identical nucleotides or amino acids in the compared nucleotide or amino acid sequence by a sequence analysis program as exemplified below.

The present invention includes an isolated nucleic acid molecule encoding aldehyde dehydrogenase which comprises a polynucleotide being at least 95% identical to the polynucleotide selected from the group consisting of (a) nucleotides 258–2084 of SEQ ID NO: 1, (b) nucleotides 351–2084 of SEQ ID NO: 1, (c) nucleotides 258–1955 of SEQ ID NO: 1, and (d) nucleotides 351–1955 of SEQ ID NO: 1.

It is another aspect of the present invention to provide an isolated nucleic acid molecule encoding aldehyde dehydrogenase which comprises a polynucleotide selected from the group consisting of (a) a polynucleotide encoding the polypeptide having the amino acid sequence of SEQ ID NO: 2, (b) a polynucleotide encoding the polypeptide consisting of amino acids 32–609 of SEQ ID NO: 2, (c) a polynucleotide encoding the polypeptide consisting of amino acids 1–566 of SEQ ID NO: 2, and (d) a polynucleotide encoding the polypeptide consisting of amino acids 32–566 of SEQ ID NO: 2. Also included are proteins having SNDH activity and which are derived from a protein mentioned above by substitution, deletion, insertion or addition of one or more amino acid(s) in the amino acid sequences mentioned above.

Functional derivatives as another aspect of the present invention are defined on the basis of the amino acid sequences of the present invention by addition, insertion, deletion and/or substitution of one or more amino acid residues of such sequences wherein such derivatives still have the SNDH activity measured by an assay known in the art or specifically described herein. Such functional derivatives can be made either by chemical peptide synthesis known in the art or by recombinant techniques on the basis of the DNA sequences as disclosed herein by methods known in the state of the art. Amino acid exchanges in proteins and peptides which do not generally alter the activity of such molecules are known in the state of the art.

In particular embodiments of the present invention, conservative substitutions of interest occur as follows: as example substitutions, Ala to Val/Leu/Ile, Arg to Lys/Gln/Asn, Asn to Gln/His/Lys/Arg, Asp to Glu, Cys to Ser, Gln to Asn, Glu to Asp, Gly to Pro/Ala, His to Asn/Gln/Lys/Arg, Ile to Leu/Val/Met/Ala/Phe/norLeu, Lys to Arg/Gln/Asn, Met to Leu/Phe/Ile, Phe to Leu/Val/Ile/Ala/Tyr, Pro to Ala, Ser to Thr, Thr to Ser, Trp to Tyr/Phe, Tyr to Trp/Phe/Thr/Ser, and Val to Ile/Leu/Met/Phe/Ala/norLeu are reasonable. As preferred examples, Ala to Val, Arg to Lys, Asn to Gln, Asp to Glu, Cys to Ser, Gln to Asn, Glu t Asp, Gly to Ala, His to Arg, Ile to Leu, Leu to Ile, Lys to Arg, Met to Leu, Phe to Leu, Pro to Ala, Ser to Thr, Thr to Ser, Trp to Tyr, Tyr to Phe, and Val to Leu are reasonable. If such substitutions result in a change in biological activity, then more substantial changes, denominated exemplary substitutions described above, are introduced and the products screened.

Furthermore the present invention is directed to polynucleotides encoding polypeptides having the SNDH activity as disclosed in the sequence listing as SEQ ID NO: 2 as well as the complementary strands, or those which include these sequences, DNA sequences or fragments thereof, and DNA sequences, which hybridize under standard conditions with such sequences but which encode for polypeptides having exactly the same amino acid sequence.

Thus, the present invention provides an isolated nucleic acid molecule encoding a polypeptide having aldehyde dehydrogenase activity, wherein the complement of said nucleic acid molecule hybridizes under standard conditions with a nucleic acid molecule as described above. It is an aspect of the invention to provide an isolated nucleic acid molecule encoding a polypeptide having aldehyde dehydrogenase activity, wherein said nucleic acid molecule hybridizes under standard conditions to the complementary strand of a nucleic acid molecule encoding (i) aldehyde dehydrogenase which comprises a polynucleotide being at least 95% identical to the nucleotide sequence of SEQ ID NO: 1; (ii) aldehyde dehydrogenase which comprises a polynucleotide being at least 95% identical to the polynucleotide selected from the group consisting of (a) nucleotides 258–2084 of SEQ ID NO: 1, (b) nucleotides 351–2084 of SEQ ID NO: 1, (c) nucleotides 258–1955 of SEQ ID NO: 1, and (d) nucleotides 351–1955 of SEQ ID NO: 1; and (iii) aldehyde dehydrogenase which comprises a polynucleotide selected from the group consisting of (a) a polynucleotide encoding the polypeptide having the amino acid sequence of SEQ ID NO: 2, (b) a polynucleotide encoding the polypeptide consisting of amino acids 32–609 of SEQ ID NO: 2, (c) a polynucleotide encoding the polypeptide consisting of amino acids 1–566 of SEQ ID NO: 2, and (d) a polynucleotide encoding the polypeptide consisting of amino acids 32–566 of SEQ ID NO: 2.

"Standard conditions" for hybridization mean in this context the conditions which are generally used by a person skilled in the art to detect specific hybridization signals, or preferably so called stringent hybridization conditions used by a person skilled in the art.

Thus, as used herein, the term "stringent hybridization conditions" means that hybridization will occur if there is 95% and preferably at least 97% identity between the sequences. Stringent hybridization conditions are, e.g., conditions under over night incubation at 42° C. using a digoxygenin (DIG)-labeled DNA probe (constructed by using a DIG labeling system; Roche Diagnostics GmbH, 68298 Mannheim, Germany) in a solution comprising 50% formamide, 5×SSC (150 mM NaCl, 15 mM trisodium citrate), 0.2% sodium dodecyl sulfate, 0.1% N-lauroylsarcosine, and 2% blocking reagent (Roche Diagnostics GmbH), followed by washing the filters in 0.1×SSC at about 60° C.

This invention is also directed to a recombinant vector, i.e., an expression vector, comprising such a nucleic acid molecule as mentioned above. An expression vector of the present invention is one which functions in a suitable host cell. Preferred vectors for the expression of the nucleic acid molecules of the present invention are vectors or derivatives thereof which are selected from the group consisting of pQE, pUC, pBluescript II, pACYC177, pACYC184, pVK100, and RSF1010.

A suitable host cell for expression of the nucleotide sequences of the present invention is a recombinant microorganism selected from the group consisting of bacteria, yeast, and plant cells. Preferably, the microorganism is selected from the group consisting of *Gluconobacter, Acetobacter, Pseudomonas, Acinetobacter, Klebsiella* and *Escherichia*. An example of such a preferred microorganism is *E. coli*. A more preferred host cell belongs to *Gluconobacter oxydans,* most preferably *G. oxydans* DSM 4025 (FERM BP-3812), which had been deposited on Mar. 17, 1987 under the conditions of the Budapest Treaty at the Deutsche Sammlung von Mikroorganismen und Zellkulturen GmbH, Braunschweig, Germany.

The microorganism "*Gluconobacter oxydans*" also includes synonyms or basonyms of such species having the same physico-chemical properties, as defined by the International Code of Nomenclature of Prokaryotes.

Thus, the present invention is directed to a recombinant microorganism which is transformed with the expression vector as described above or which comprises a nucleic acid molecule as described above integrated into its chromosomal DNA.

A wide variety of host/vector combinations maybe used for cloning the double stranded nucleotide sequences of the present invention. As *E. coli* is a preferred host cell, any vectors usually used in *E. coli* are useful for the present invention. Such vectors include, but are not limited to, pQE vectors which can express His-tagged recombinant proteins (QIAGEN K.K., Tokyo, Japan), pBR322 or its derivatives including pUC18 and pBluescript II (Stratagene Cloning Systems, California, USA), pACYC177 and pACYC184 and their derivatives, and a vector derived from a broad host range plasmid such as RK2 and RSF1010. Thus, the expression vector used in the present invention is derived from pQE-plasmids, pUC-plasmids, pBluescript II, pACYC177, pACYC184, and their derivative plasmids, and a broad host range plasmid such as pVK100 and RSF1010.

As used herein, "expression vector" means a cloning vector which is capable of enhancing the expression of a gene that has been cloned into it, after transformation into a suitable host. The cloned gene is usually placed under the control of (i.e., operably linked to) certain control sequences such as promoter sequences. Promoter sequences may be either constitutive or inducible.

As used herein, "cloning vector" means a plasmid or phage DNA or other DNA sequence which is able to replicate autonomously in a host cell, and which is characterized by a single or a small number of restriction endonuclease recognition sites at which such DNA sequences may be cut in a determinable fashion without loss of an essential biological function of the vector, and into which a DNA fragment may be introduced in order to bring about its replication and cloning. The cloning vector may further contain a marker suitable for use in the identification of cells transformed with the cloning vector. Such markers provide, e.g., tetracycline or ampicillin resistance.

As used herein, a "recombinant vector" includes any cloning or expression vector which contains the desired cloned gene(s).

As used herein, "expression" refers to the process by which a polypeptide is produced from a structural gene. The process involves transcription of the gene into mRNA and the translation of such mRNA into polypeptide(s).

As used herein, "recombinant microorganism" includes a recombinant host which may be any prokaryotic or eukaryotic cell that contains the desired cloned gene(s) on an expression or cloning vector. This term also includes those prokaryotic or eukaryotic cells that have been genetically engineered to contain the desired gene(s) in the chromosome or genome of said microorganism.

As used herein, "host" includes any prokaryotic or eukaryotic cell that is the recipient of a replicable expression vector or cloning vector. A "host", as the term is used herein, also includes prokaryotic or eukaryotic cells that can be genetically engineered by well known techniques to contain desired gene(s) on its chromosome or genome. Examples of such hosts are known to the skilled artisan.

To construct a recombinant microorganism carrying recombinant DNA, e.g., a recombinant vector, various gene transfer methods including, but not limited to, transformation, transduction, conjugal mating or electroporation can be used. These methods are well-known in the field of molecular biology. Conventional transformation systems can be used for *Gluconobacter, Acetobacter, Pseudomonas, Acinetobacter, Klebsiella* or *Escherichia*. A transduction system can also be used for *E. coli*. Conjugal mating systems can be widely used in Gram-positive and Gram-negative bacteria including *E. coli, P. putida*, and *Gluconobacter*. An example of conjugal mating is disclosed in WO 89/06,688. The conjugation can occur in liquid medium or on a solid surface. Examples for a suitable recipient for SNDH production include microorganisms of *Gluconobacter, Acetobacter, Pseudomonas, Acinetobacter, Klebsiella* or *Escherichia*. To the recipient for conjugal mating, a selective marker may be added, e.g., resistance against nalidixic acid or rifampicin. Natural resistance can also be used, e.g., resistance against polymyxin B is useful for many *Gluconobacters*.

Preferred vectors useful for the present invention are broad-host-range vectors such as a cosmid vector like pVK100 and its derivatives and RSF1010. Copy number and stability of the vector should be carefully considered for stable and efficient expression of the cloned nucleic acid molecules and also for efficient cultivation of the host cell carrying said cloned molecules. Nucleic acid molecules containing transposable elements such as Tn5 can also be used to introduce the desired DNAs into the preferred host, especially on a chromosome. Nucleic acid molecules containing any DNAs isolated from the preferred host together with the nucleotide sequences of the present invention are also useful to introduce the nucleotide sequences of the present invention into the preferred host cell, especially on a chromosome. Such nucleic acid molecules can be transferred to the preferred host by applying any of a conventional method, e.g., transformation, transduction, conjugal mating or electroporation, which are well known in the art, considering the nature of the host cell and the nucleic acid molecule.

The nucleotide sequences including the SNDH gene provided in this invention are ligated into a suitable vector containing a regulatory region such as a promoter, a ribosomal binding site, and a transcriptional terminator operable in the host cell described above with a method well-known in the art to produce a suitable expression vector.

To express the desired gene/nucleotide sequence isolated from *G. oxydans* DSM 4025 efficiently, various promoters can be used; e.g., the original promoter of the gene, promoters of antibiotic resistance genes such as kanamycin resistant gene of Tn5, ampicillin resistant gene of pBR322, and beta-galactosidase of *E. coli* (lac), trp-, tac-, trc-promoter, promoters of lambda phage and any promoters which are functional in a host cell. For this purpose, the host cell can be selected from the group consisting of bacteria, yeast, and plant cells. Preferably, the host cell belongs to the genera *Gluconobacter, Acetobacter, Pseudomotias, Acinetobacter, Klebsiella* or *Escherichia*.

For expression, other regulatory elements, such as a Shine-Dalgarno (SD) sequence (e.g., AGGAGG, including natural and synthetic sequences operable in the host cell) and a transcriptional terminator (inverted repeat structure including any natural and synthetic sequence operable in the host cell) which are operable in the host cell (into which the coding sequence will be introduced to provide a recombinant cell of this invention) can be used with the above described promoters.

For the expression of polypeptides which are located in the periplasmic space, like the SNDH protein of the present invention, a signal peptide, which contains usually 15 to 50 amino acid residues and is totally hydrophobic, is preferably associated. A DNA encoding a signal peptide can be selected from any natural and synthetic sequence operable in the desired host cell. A putative signal peptide containing amino acid residues 1–31 of SEQ ID NO: 2 was also found in the protein expressed by the SNDH gene of the present invention (SEQ ID NO: 4).

Unless otherwise mentioned, all amino acid sequences determined by sequencing the purified SNDH protein herein were determined using an automated amino acid sequencer (such as model 470A, Perkin-Elmer Applied Biosystems).

Unless otherwise indicated, all nucleotide sequences determined by sequencing a DNA molecule herein were determined using an automated DNA sequencer (such as the model ALF express II, Amersham Pharmacia Biotech), and all amino acid sequences of polypeptides encoded by DNA molecules determined herein were predicted by translation of the DNA sequence determined as above. Therefore, as it is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The invention provides an isolated nucleic acid molecule encoding the enzyme (SNDH). Methods and techniques designed for the manipulation of isolated nucleic acid molecules are well known in the art. Methods for the isolation, purification, and cloning of nucleic acid molecules, as well as methods and techniques describing the use of eukaryotic and prokaryotic host cells and nucleic acid and protein expression therein, are known to the skilled person.

Briefly, the SNDH gene, the DNA molecule containing said gene, the recombinant expression vector and the recombinant microorganism used in the present invention can be obtained by the following steps:

(1) isolating chromosomal DNA from *G. oxydans* DSM 4025 and constructing a gene library with the chromosomal DNA in an appropriate host cell, e.g., *E. coli*;

(2) cloning the SNDH gene from the chromosomal DNA by colony-, plaque-, or Southern-hybridization, PCR (polymerase chain reaction) cloning, western-blot analysis or other techniques known in the art;

(3) determining the nucleotide sequence of the SNDH gene obtained as above by conventional methods to select a DNA molecule containing said SNDH gene and constructing a recombinant expression vector on which the SNDH gene can be expressed efficiently;

(4) constructing recombinant microorganisms carrying the SNDH gene by an appropriate method for introducing DNA into a host cell, e.g., transformation, transduction, conjugal transfer and/or electroporation, which host cell thereby becomes a recombinant microorganism of this invention.

The materials and techniques used in the above aspect of the present invention are exemplified in detail as follows:

A total chromosomal DNA can be purified by a procedure well known in the art. The desired gene can be cloned in either plasmid or phage vectors from a total chromosomal DNA typically by either of the following illustrative methods:

(i) The partial amino acid sequences are determined from the purified proteins or peptide fragments thereof. Such whole protein or peptide fragments can be prepared by the isolation of such a whole protein or by peptidase-treatment from the gel after SDS-polyacrylamide gel electrophoresis. Thus obtained protein or fragments thereof are applied to protein sequencer such as Applied Biosystems automatic gas-phase sequencer 470A. The amino acid sequences can be utilized to design and prepare oligonucleotide probes and/or primers with DNA synthesizer such as Applied Biosystems automatic DNA sequencer 381A. The probes can be used for isolating clones carrying the target gene from a gene library of the strain carrying the target gene by means of Southern-, colony- or plaque-hybridization.

(ii) Alternatively, for the purpose of selecting clones expressing a target protein from the gene library, immunological methods with antibodies prepared against the target protein can be applied.

(iii) The DNA fragment of the target gene can be amplified from the total chromosomal DNA by PCR method with a set of primers, i.e., two oligonucleotides synthesized according to the amino acid sequences determined as above. Then a clone carrying the target-whole gene can be isolated from the gene library constructed, e.g., in *E. coli*, by Southern-, colony-, or plaque-hybridization with the PCR product obtained above as probe.

DNA sequences which can be made by PCR by using primers designed on the basis of the DNA sequences disclosed herein by methods known in the art are also an object of the present invention.

Above mentioned antibodies can be prepared with the purified SNDH proteins, the purified recombinant SNDH proteins such as His-tagged SNDH expressed in *E. coli*, or its peptide fragment as an antigen.

Once a done carrying the desired gene is obtained, the nucleotide sequence of the target gene can be determined by a well known method such as dideoxy chain termination method with M13 phage.

Figure 2:
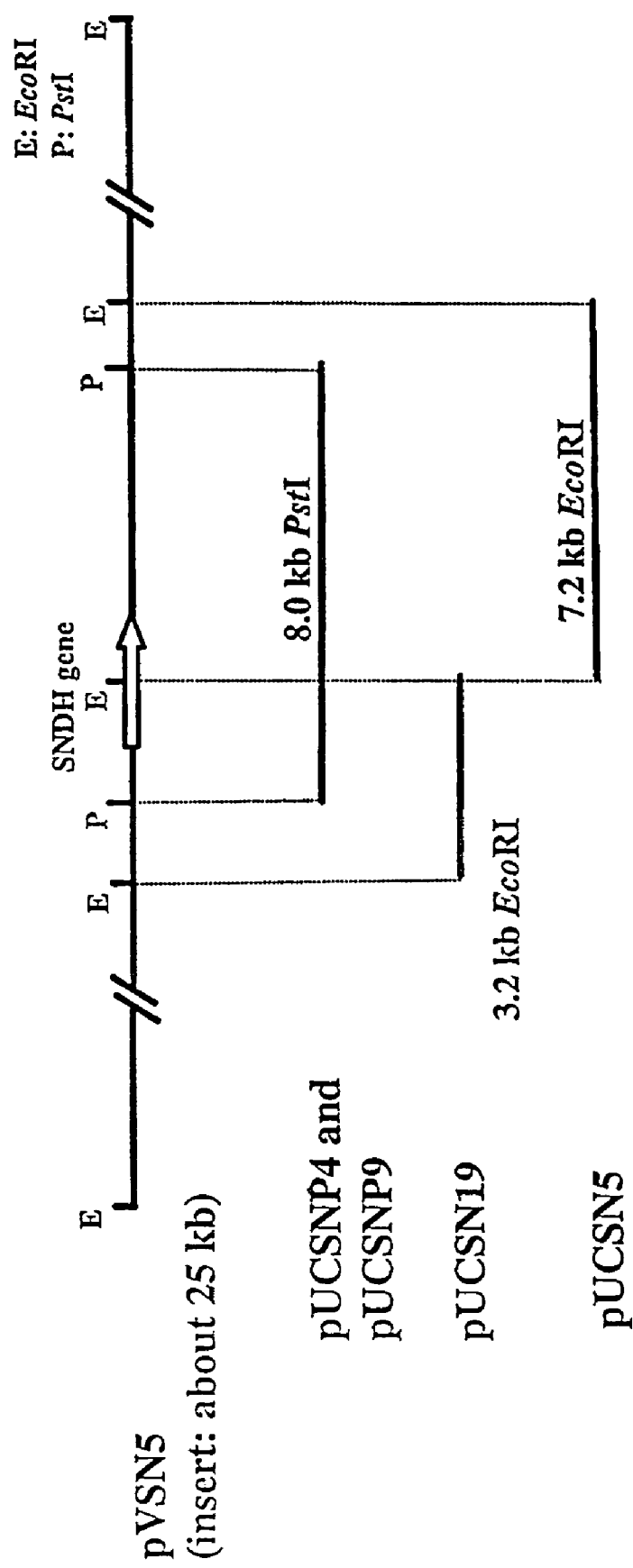
FIG. 2 illustrates the restriction map of the SNDH and ORF-A genes cloned into cosmid pVSN5 as well as cloning of insert DNA of different sizes into pUC plasmids pUCSNP4, pUCSNP9, pUCSN19, and pUCSN5. In the physical map of pVSN5, the arrow filled in gray shows the SNDH gene.

The gene of the present invention encodes an SNDH enzyme of 578 amino acid residues (SEQ ID NO: 5 consisting of amino acids 32–609 of SEQ ID NO: 2) together with a putative signal peptide of 31 amino acid residues (SEQ ID NO: 4 consisting of amino acids 1–31 of SEQ ID NO: 2) as depicted in FIG. 2. In terms of nucleotide sequences, the coding region of the SNDH gene encompasses nucleotides 258–2087 of SEQ ID NO: 1 and includes the coding sequences for a putative signal peptide (nucleotides 258–350 of SEQ ID NO: 1) and the stop codon (nucleotides 2085–2087 of SEQ ID NO: 1). Thus, the nucleotide sequence without the stop codon is the nucleotide sequence from position 258–2084 of SEQ ID NO: 1, and additionally without the signal sequence the nucleotide sequence encompasses nucleotides 351–2084 of SEQ ID NO: 1.

The nucleic acid molecules as disclosed in the present invention can be used in a recombinant microorganism for the production of 2-KGA and/or vitamin C. The recombinant microorganism, which is selected from *Gluconobacter, Acetobacter, Pseudomonas, Acinetobacter, Klebsiella* and *Escherichia*, may be cultured in an aqueous medium supplemented with appropriate nutrients under aerobic conditions. The cultivation may be conducted at a pH of 4.0 to 9.0, preferably 6.0 to 8.0. The cultivation period varies depending on the pH, temperature and nutrient medium to be used, and is preferably about 1 to 5 days. The preferred temperature range for carrying out the cultivation is from about 13° C. to about 36° C., preferably from about 18° C. to about 33° C. It is usually required that the culture medium contains such nutrients as assimilable carbon sources, e.g., glycerol, D-mannitol, D-sorbitol, erythritol, ribitol, xylitol, arabitol, inositol, dulcitol, D-ribose, D-fructose, D-glucose, and sucrose, preferably D-sorbitol, D-mannitol, and glycerol; and digestible nitrogen sources such as organic substances, e.g., peptone, yeast extract, baker's yeast, urea, amino acids, and corn steep liquor. Various inorganic substances may also be used as nitrogen sources, e.g., nitrates and ammonium salts. Furthermore, the culture medium usually contains inorganic salts, e.g., magnesium sulfate, potassium phosphate, and calcium carbonate. The cultivation is carried out in appropriate equipment such as jar fermentors, flasks, or tubes. The recombinant microorganism is either transformed with an expression vector containing the nucleic acid molecules as above or comprises the nucleic acid molecule of the present invention integrated into its chromosomal DNA.

An appropriate sugar compound used as substrate for the production of 2-KGA and/or vitamin C is L-sorbosone. The metabolic pathway for 2-KGA and vitamin C goes from D-sorbitol via L-sorbose to L-sorbosone, which is then converted to 2-KGA and/or vitamin C. Thus, the direct substrate for both products is L-sorbosone.

Thus, it is an aspect of the present invention to provide a process for the production of 2-KGA and/or vitamin C from L-sorbosone comprising (a) propagating or cultivating the recombinant microorganism, which is either transformed with an the present invention or which comprises the nucleic add molecules of the present invention integrated into its chromosomal DNA, in an appropriate culture medium and (b) recovering and separating 2-KGA and/or vitamin C from said culture medium It is one embodiment to provide a process for the production of vitamin C and/or 2-KGA from L-sorbosone comprising (a) propagating a recombinant organism in an appropriate culture medium, wherein the nucleic acid molecule as of the present invention is heterologously introduced to said recombinant organism, and (b) recovering and separating vitamin C and/or 2-KGA from said culture medium.

The present invention provides recombinant SNDH. One can increase the production yield of the SNDH enzyme by introducing the SNDH gene provided by the present invention into a host cell including *G. oxydans* DSM 4025. One can also produce more efficiently the SNDH proteins in a host cell selected from a group consisting of *Gluconobacter, Acetobacter, Pseudomonas, Acinetobacter, Klebsiella* and *Escherichia* by using the SNDH gene of the present invention. The microorganism may be cultured as described above.

An embodiment for the isolation and purification of the recombinant SNDH from the microorganism after the cultivation is briefly described hereinafter: cells are harvested from the liquid culture broth by centrifugation or filtration. The harvested cells are washed with water, physiological saline or a buffer solution having an appropriate pH. The washed cells are suspended in the buffer solution and disrupted by means of a homogenizer, sonicator or French press, or by treatment with lysozyme to give a solution of disrupted cells. The recombinant SNDH is isolated and purified from the cell-free extract of disrupted cells, preferably from the cytosol fraction of the microorganism. The recombinant SNDH can be immobilized on a solid carrier for solid phase enzyme reaction.

The invention is further directed to a process for the production of 2-KGA from L-sorbosone comprising (a) cultivating a microorganism belonging to *Gluconobacter oxydans* DSM 4025 in an appropriate culture medium, wherein the gene encoding aldehyde dehydrogenase represented by SEQ ID NO: 2 is disrupted in said microorganism, and (b) recovering and separating 2-KGA from said culture medium. The disruption may take place anywhere in the gene, resulting in a non-functioning of the encoded enzyme.

Thus, a process is provided for the production of 2-KGA via L-sorbosone from an appropriate sugar compound comprising (a) propagating a microorganism belonging to *Gluconobacter oxydans* DSM 4025 in an appropriate culture medium, wherein the gene encoding aldehyde dehydrogenase is disrupted in said microorganism, said aldehyde dehydrogenase being encoded by (i) a polynucleotide being at least 95% identical to the nucleotide sequence of SEQ ID NO: 1; (ii) a polynucleotide being at least 95% identical to the polynucleotide selected from the group consisting of (a) nucleotides 258–2084 of SEQ ID NO: 1, (b) nucleotides 351–2084 of SEQ ID NO: 1, (c) nucleotides 258–1955 of SEQ ID NO: 1, and (d) nucleotides 351–1955 of SEQ ID NO: 1; and (iii) a polynucleotide selected from the group consisting of (a) a polynucleotide encoding the polypeptide having the amino add sequence of SEQ ID NO: 2, (b) a polynucleotide encoding the polypeptide consisting of amino adds 32–609 of SEQ ID NO: 2, (c) a polynucleotide encoding the polypeptide consisting of amino acids 1–566 of SEQ ID NO: 2, and (d) a polynucleotide encoding the polypeptide consisting of amino acids 32–566 of SEQ ID NO: 2. The resulting 2-KGA is further recovered and isolated from said culture medium.

In one embodiment, the invention provides a process for the disruption of the SNDH gene by classical mutagenesis with agents such as UV-irradiation or chemical treatment by any mutation reagents, e.g., N-methyl-N'-nitro-N-nitrosoguanidine (NTG), ICR170 or acrydine orange, in vivo as well as in vitro.

In another embodiment, the invention provides a process for the disruption of the SNDH gene by DNA recombination techniques such as transposon insertion or site directed mutagenesis by PCR, in vivo as well as in vitro.

In another embodiment, the invention provides a process for producing 2-KGA using the disruptants described above by fermentation from an appropriate substrate, i.e., a sugar compound, which is selected from the group consisting of L-sorbosone, D-glucose, D-sorbitol, and L-sorbose. The process takes place in appropriate equipment such as jar fermentors, flasks, or tubes. Furthermore, the invention provides a process for producing 2-KGA using a cell free extract of the disruptants described above by incubation from an appropriate substrate, e.g., L-sorbosone, D-glucose, L-sorbose, and D-sorbitol, in appropriate equipment such as a bioreactor.

The present invention provides recombinant SNDH. Furthermore, it is directed to a process for the production of aldehyde dehydrogenase comprising (a) cultivating a recombinant microorganism comprising a nucleic acid molecule encoding aldehyde dehydrogenase which comprises (i) a polynucleotide being at least 95% identical to the nucleotide sequence of SEQ ID NO: 1; (ii) a polynucleotide being at least 95% identical to the polynucleotide selected from the group consisting of (a) nucleotides 258–2084 of SEQ ID NO: 1, (b) nucleotides 351–2084 of SEQ ID NO: 1, (c) nucleotides 258–1955 of SEQ ID NO: 1, and (d) nucleotides 351–1955 of SEQ ID NO: 1; and (iii) a polynucleotide selected from the group consisting of (a) a polynucleotide encoding the polypeptide having the amino acid sequence of SEQ ID NO: 2, (b) a polynucleotide encoding the polypeptide consisting of amino acids 32–609 of SEQ ID NO: 2, (c) a polynucleotide encoding the polypeptide consisting of amino acids 1–566 of SEQ ID NO: 2, and (d) a polynucleotide encoding the polypeptide consisting of amino acids 32–566 of SEQ ID NO: 2; wherein said microorganism is cultivated in an appropriate culture medium and (b) wherein said aldehyde dehydrogenase is recovered and separated from said culture medium.

EXAMPLE 1

Amino Acid Sequencing From the N-terminus of SNDH

The partial amino acid sequence of the N-terminal 75 kDa subunit of the SNDH protein was determined. About 10 µg of the SDS-treated purified SNDH consisting of 75 kDa subunits was subjected to SDS-PAGE, and the protein band was electroblotted onto a PVDF membrane. The protein blotted on the membrane was soaked in a digestion buffer (100 mM potassium phosphate buffer, 5 mM dithiothreitol, 10 mM EDTA, pH 8.0) and incubated with 5.04 µg of pyroglutamate aminopeptidase (SIGMA, USA) at 30° C. for 24 hours. After incubation, the membrane was washed with deionized water and subjected to N-terminal amino acid sequencing using an automated amino acid sequencer (ABI model 490, Perkin Elmer Corp., Conn., USA). As a result, 14 residues of the N-terminal amino acid sequence were obtained as illustrated in SEQ ID NO: 3.

EXAMPLE 2

Cloning of Partial SNDH Gene by PCR

Amplification of the partial SNDH gene fragment was carried out by PCR with chromosomal DNA of *G. oxydans*

DSM 4025 (FERM BP-3812) and degenerated oligonucleotide DNA primers, P11 (SEQ ID NO: 6) and P12 (SEQ ID NO: 7). Both primers were degenerated DNA mixtures having bias for *Gluconobacter* codon usage. The PCR was performed with thermostable taq polymerase (TAKARA Ex Taq™, Takara Shuzo Co., Ltd., Seta 3-4-1, Otsu, Shiga, 520-2193, Japan), using a thermal cycler (Gene Amp PCR System 2400-R, PE Biosystems, 850 Lincoln Centre Drive, Foster City, Calif. 94404, USA). The reaction mixture (25 µl) consisted of 200 µM of dNTPs, 50 pmol of each primer (24~48 degeneracy), 5 ng of the chromosomal DNA, and 1.25 units of the DNA polymerase in the buffer provided from the supplier. The reaction was carried out with 5 cycles of denaturation step at 94° C. for 30 sec, annealing step at 37° C. for 30 sec, synthesis step at 70° C. for 1 min followed by 25 cycles of denaturation step at 94° C. for 30 sec, annealing step at 50° C. for 30 sec) synthesis step at 70° C. for 1 min. As a result, a 41 bp DNA fragment was specifically amplified and cloned into vector pCR 2.1-TOPO (Invitrogen, 1600 Faraday Avenue Carlsbad, Calif. 92008, USA) to obtain a recombinant plasmid pMTSN2. The nucleotide sequence of the cloned 41 bp DNA fragment which encodes an N-terminal partial amino acid sequence of the mature SNDH protein was confirmed by dideoxy-chain termination method (F. Sanger et al, Proc. Natl. Acad. Sci. USA, 74, 5463–5467, 1977).

EXAMPLE 3

Complete Cloning of the SNDH Gene (1) Construction of a gene library of *G. oxydans* DSM 4025

The chromosomal DNA of *G. oxydans* DSM 4025 was prepared from cells grown on M agar medium containing 5% D-mannitol, 1.75% corn steep liquor, 5% baker's yeast, 0.25% $MgSO_4.7H_2O$, 0.5% $CaCO_3$ (Practical Grade), 0.5% urea, and 2.0% agar (pH 7.0), for 4 days at 27° C. The chromosomal DNA (4 µg) was partially digested with 4 units of EcoR I in 20 µl of reaction mixture. A portion (8 µl) of the sample containing partially-digested DNA fragments was separated by an electrophoresis using 1% agarose gel. Fragments ranging from 15 to 35 kb were cut out and chemically melted to recover the fragments using QIAEX II (QIAGEN Inc., 28159 Avenue Stanford, Valencia, Calif. 91355, USA). The objective DNA fragments recovered were suspended in $H_2O$. On the other hand, 2 µg of a cosmid vector pVK100 was completely digested with EcoR I and dephosphorylated of the 5'-ends by treating with bacterial alkaline phosphatase (*E. coli* C75) (Takara Shuzo). The treated pVK100 (220 ng) was ligated with the 15–35 kb EcoR I fragments (1 µg) using a ligation kit (Takara Shuzo) in 36 µl of reaction mixture. The ligated DNA which had been ethanol precipitated and resolved in appropriate volume of TE buffer (10 mM Tris-HCl pH 8.0, 1 mM EDTA) was used for in vitro packaging (Gigapack III Gold Packaging Extract, Stratagene, 11011 North Torrey Pines Road, La Jolla, Calif. 92037, USA) to infect *E. coli* VCS257, a host strain for the genomic library. As a result, totally 400,000–670,000 clones containing about 25 kb-inserted DNA fragments were obtained.

(2) Complete cloning of the SNDH gene by colony hybridization

The probe that would be used for screening of the cosmid library described above to detect clones carrying the complete SNDH gene by colony hybridization method, was constructed. The 41 bp DNA fragment encoding the N-terminal amino acid sequence of SNDH was amplified and labeled by PCR-DIG labeling method (Roche Molecular Systems Inc., 1145 Atlantic Avenue, Alabama, Calif. 94501, USA). PCR with plasmid pMTSN2 DNA as a template and oligonucleotide DNA primers, P13 (SEQ ID NO: 8) and P14 (SEQ ID NO: 9), was performed with thermostable taq polymerase (TAKARA Ex Taq™, Takara Shuzo Co., Ltd.), using a thermal cycler (Gene Amp PCR System 2400-R, PE Biosystems). The reaction was carried out with 25 cycles of denaturation step at 94° C. for 30 sec, annealing step at 55° C. for 30 sec, synthesis step at 70° C. for 1 min. Using the DIG-labeled probe, screening of the cosmid library (about 1,000 clones) by colony hybridization and chemiluminescent detection according to the method provided from the supplier (Roche Molecular Systems Inc., USA) was carried out. As a result, 3 positive clones were isolated and one of them was designated pVSN5, which carried about 25 kb insert DNA in pVK100 vector. From this, 25 kb DNA insert fragments of different sizes were further subcloned into pUC18 vectors (FIG. 2): (1) a 3.2 kb EcoR I fragment comprising the upstream portion (the N-terminal part) of the SNDH gene resulting in pUCSN19, (2) a 7.2 kb EcoR I fragment comprising the downstream portion (the C-terminal part) of the SNDH gene resulting in pUCSN5, and (3) a 1.8 kb Pst I fragment comprising the intact or complete SNDH gene resulting in pUCSNP4 and pUCSNP9, respectively. Note that the inserts in pUSNP4 and pUSNP9 are the same but in opposite directions.

(3) Nucleotide sequencing of the SNDH gene

Figure 1:
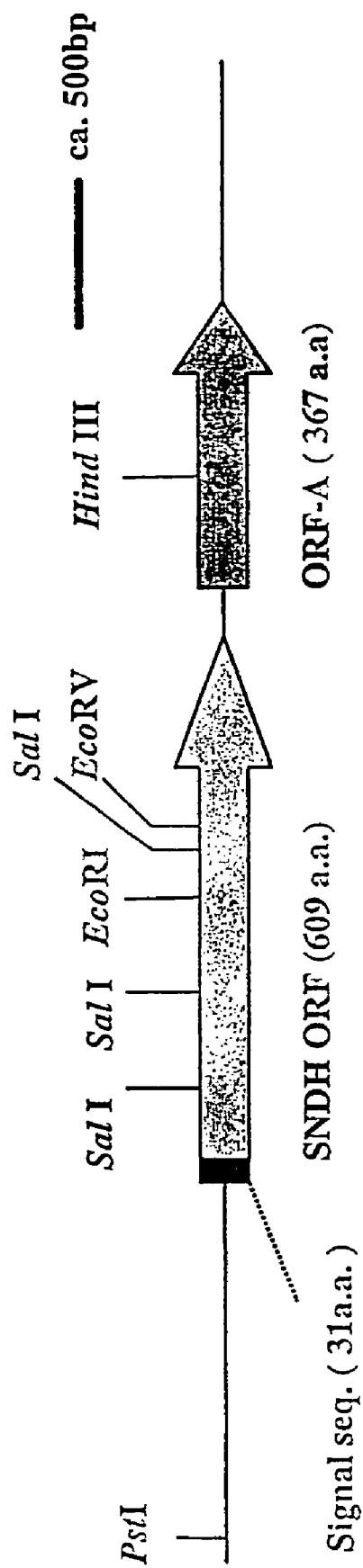
FIG. 1 illustrates the gene encoding a protein having aldehyde dehydrogenase activity of the present invention. The restriction map of the SNDH gene and ORF-A gene is given, wherein ORF means open reading frame and Signal seq. means the putative signal peptide sequence of the SNDH gene.

Plasmids pUCSN19, pUCSN5, and pUCSNP4 were used for nucleotide sequencing of a region including the SNDH gene or gene fragments. The determined nucleotide sequence (SEQ ID NO: 1 with 3,408 bp) revealed that the ORF of the SNDH gene (1,827 bp; nucleotides 258–2084 of SEQ ID NO: 1) encoded a polypeptide of 609 amino acid residues (SEQ ID NO: 2). An additional ORF, ORF-A, was found downstream of the SNDH ORF as illustrated in FIG. 1. ORF-A (1,101 bp; nucleotides 2214–3314 of SEQ ID NO: 1) encoded a polypeptide of 367 amino acids.

In the ORF of the SNDH gene, a signal peptide-like sequence (SEQ ID NO: 4 with 31 amino acids) is possibly included in the deduced amino acid sequence, which contains (i) many hydrophobic residues, (ii) positively-charged residues close to the N-terminus and (iii) Ala-Xaa-Ala motif for cleavage site of the signal sequence. The putative ribosome-binding site (Shine-Dalgarno, SD, sequence) for the SNDH gene was located at 6 bp upstream of the initiation codon (AGGAGA at nucleotide position 247–252 of SEQ ID NO: 1). Furthermore, a motif (Cys-Xaa-Xaa-Cys-His) defined as heme c binding site was found at position 530–534 of SEQ ID NO: 2. From the genetically analysis as shown above, the SNDH protein is thought to be one of quinohemoproteins.

A homology search for the SNDH gene using the program of FASTA in GCG (Genetics Computer Group, Madison, Wis., USA) revealed that Arg227, Asn228, Gln230, Gly246, and Asp251 of SEQ ID NO: 5 correspond to several highly conserved residues in the presumed active site of *A. calcoaceticus* GDH-B protein described by Oubrie et al. [J. Mol. Biol. 289:319–333 (1999)].

EXAMPLE 4

Expression of the SNDH Gene in *E. coli*

Figure 3:
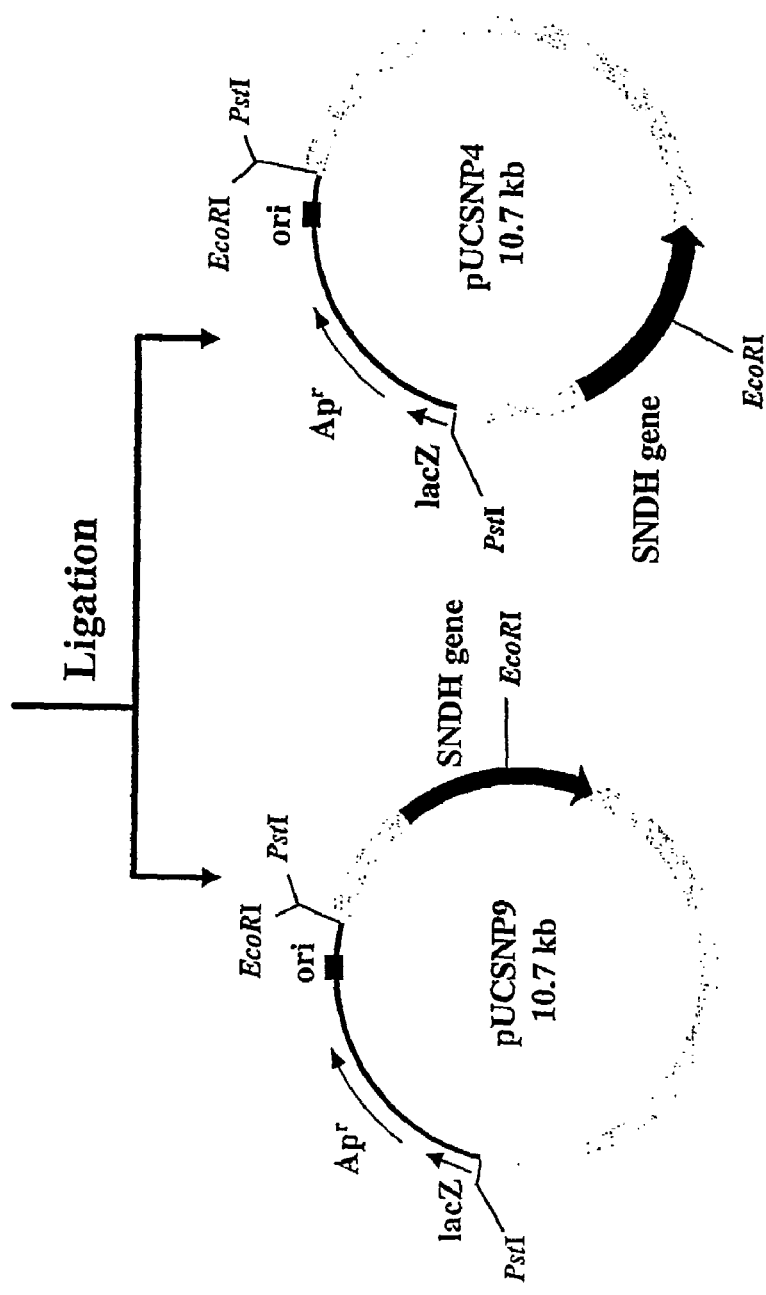
FIG. 3 shows the cloning strategy of the 8.0 kb PstI fragment including the intact SNDH gene from pVSN5 into pUC18 vectors to result in pUCSNP4 and pUCSNP9. Note that pUCSNP4 and pUCSNP9 are identical except for the direction of the insert

Plasmids pUCSNP4 and pUCSNP9 (FIG. 3), containing the 8.0 kb Pst I-fragment with the intact, i.e., complete SNDH gene, were transformed into *E. coli* JM109 to confirm the expression and the activity of the SNDH proteins.

The amount of vitamin C produced as the enzyme activity was measured at a wavelength of 264 nm by a high performance liquid chromatography system (HPLC) which was composed with a UV detector (TOSOH UV8000; Tosoh, Japan), a dualpump (TOSOH CCPE; Tosoh), an integrator (Shimadzu C-R6A; Shimadzu, Japan) and a column (YMC-Pack Polyamine-II; 4.6 mm of inner diameter [i.d.]×15 cm, YMC, U.S.A.).

The conversion activity of L-sorbosone to vitamin C by using cytosol fraction of the recombinant E. coli was tested (Table 1). Cells were cultivated in LB medium optionally supplemented with 10 μM of PQQ and 1.0 mM of $CaCl_2$. The cytosol fraction was prepared by ultracentrifugation (100,000×g, 45 min) of the cell free extract in 50 mM potassium phosphate buffer (pH 7.0). The reaction mixture (100 μl) consisted of 125 μg of cytosol fraction of the recombinant E. coli, 50 mM of L-sorbosone, 1.0 mM of phenazine mesosulfate (PMS), with or without the addition of 1.0 μM of PQQ and 1.0 mM of $CaCl_2$ as cofactots, depending on the case. The enzyme reaction was carried out at 30° C. for 30 min. The holo-SNDHs of the cells cultivated in LB medium containing 10 μM of PQQ and 1.0 mM of $CaCl_2$ produced vitamin C definitely under the defined reaction condition without the cofactors of PQQ and $CaCl_2$. By addition of the cofactors, the apo-SNDH expressed with pUCSNP4 and pUCSNP9 showed almost the same activity as those of the holo-enzyme.

TABLE 1 activity measurement of recombinant SNDH

| Microorganism | PQQ and $CaCl_2$ in the medium | Specific activity (mU/mg Protein) with PQQ and $CaCl_2$ | Specific activity (mU/mg Protein) without PQQ and $CaCl_2$ |
|---|---|---|---|
| E. coli JM109/ pUCSNP4 | + | 0.187 | 0.224 |
| E. coli JM109/ pUCSNP9 | + | 0.198 | 0.252 |
| E. coli JM109/ pUC18 | + | 0.000 | 0.000 |
| E. coli JM109/ pUCSNP4 | — | 0.155 | 0.000 |
| E. coli JM109/ pUCSNP9 | — | 0.176 | 0.000 |
| E. coli JM109/ pUC18 | — | 0.000 | 0.000 |
| G. oxydans DSM 4025 | — | 0.026 | 0.026 |

One unit (U) of the enzyme was defined as the amount of enzyme, which produces 1.0 mg of vitamin C in the defined reaction.

EXAMPLE 5

Construction and Cultivation of SNDH-gene Disruptants of G. oxydans Strains

Figure 4:
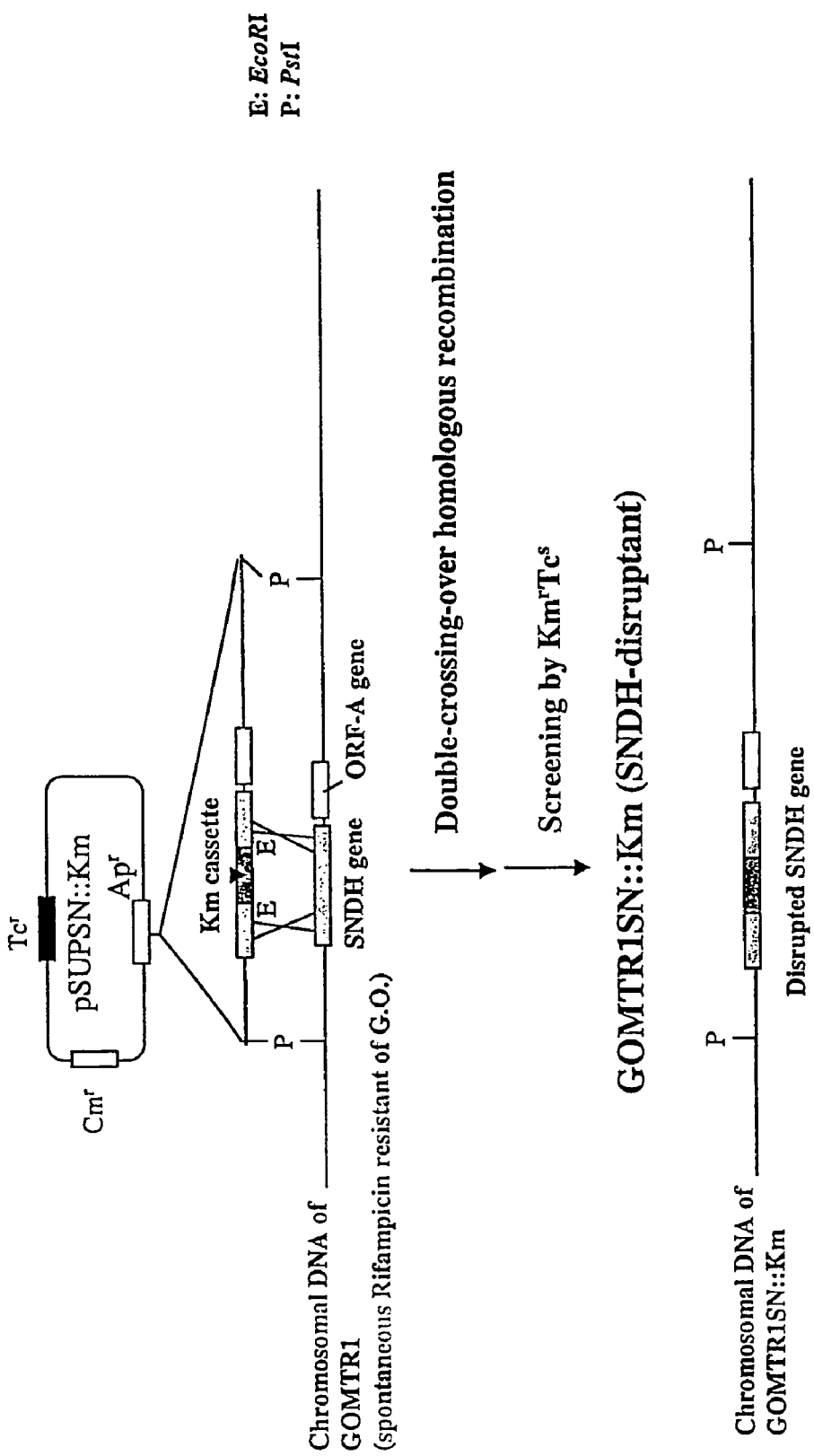
FIG. 4 shows schematically the construction of the GOMTR1SN::Km (SNDH-disruptant) by using a suicide vector plasmid having the disrupted SNDH gene with kanamycin cassette (Km). Homologous recombination between the vector plasmid and the chromosomal DNA of GOMTR1 as the parent strain at the corresponding region occurs to obtain the disruptant strains. "G.O." means *Gluconobacter oxydans*.

FIG. 4 shows the scheme for the construction of SNDH gene targeting vector, GOMTR1SN::Km (SNDH-disruptant). First, plasmid pSUPSN was constructed by a ligation of the 8.0 kb Pst I fragment containing the SNDH gene from plasmid pUCSNP4 with a suicide vector pSUP202 (for reference see Simon et al., A broad host range mobilization system for in vitro genetic engineering: transposon mutagenesis in Gram negative bacteria, Biotechnology, 1, 784–791, 1983). Second, a kanamycin-resistant-gene cassette (Km cassette) was inserted into the EcoR I site of the SNDH gene cloned in plasmid pSUPSN to obtain plasmid pSUPSN::Km ($Km^rTc^r$). Then, plasmid pSUPSN::Km was introduced into GOMTR1, which was a rifampicin (Rif) resistant derived spontaneously from wildtype G. oxydans DSM 4025 strain, to result in SNDH-null mutants ($Km^rRif^rTc^s$).

GOMTR1 was cultivated in a 200 ml flask containing 50 ml of T broth, which was composed of 30 g/l of Trypticase Soy Broth (BBL; Becton Dickinson and Company, Cockeysville, Md. 21030, USA) and 3 g/l of yeast extract (Difco; Becton Dickinson Microbiology Systems, Becton Dickinson and Company, Sparks, Md. 21152, USA) with 100 μg/ml of rifampicin at 30° C. overnight. E. coli HB101 (pRK2013) [D. H. Figurski, Proc. Natl. Acad. Sci. USA, 76, 1648–1652, 1979] and E. coli JM109 (pSUPSN::Km) were cultivated in test tubes containing 2 ml of LB medium with 50 μg/ml of kanamycin at 30° C. overnight. Cultured cells of GOMTR1, E. coli HB101 (pRK2013), and E. coli JM109 (pSUPSN::Km) were collected separately by centrifugation and each cell suspension in LB medium was mixed in the ratio of 10:1:1, respectively. Then these cell suspensions were mixed at the same volume and the mixture was spread out on a 0.45 μm nitrocellulose membrane (PROTRAN, Schleicher & Schuell GmbH, Postfach 4, D-37582 Dassel, Germany) put on an agar medium, which was composed of 5.0% mannitol, 0.25% $MgSO_4.7H_2O$, 1.75% corn steep liquor, 5.0% baker's yeast, 0.5% urea, 0.5% $CaCO_3$, and 2.0% agar, for conjugal transfer of the suicide plasmid from the E. coli donor to GOMTR1 as recipient. After cultivation at 27° C. for 1 day, the cells containing transconjugants were suspended and diluted appropriately with T broth, and spread out on the screening agar plates containing 100 μg/ml of rifampicin and 50 μg/ml of kanamycin. Finally, several transconjugants ($Km^rRif^rTc^s$) which had the disrupted SNDH gene with Km cassette were obtained.

GOMTR1 and the disruptants, GOMTR1SN::Km, were grown on an agar plate containing 8.0% L-sorbose, 0.25% $MgSO_4.7H_2O$, 1.75% corn steep liquor, 5.0% baker's yeast, 0.5% urea, 0.5% $CaCO_3$; and 2.0% agar at 27° C. for 4 days. One loopful of the cells was inoculated into 50 ml of a seed culture medium (pH 6.0) containing 4% D-sorbitol, 0.4% yeast extract, 0.05% glycerol, 0.25% $MgSO_4.7H_2O$, 1.75% corn steep liquor, 0.1% urea, and 1.5% $CaCO_3$ in a 500 ml Erlenmeyer flask, and cultivated at 30° C. with 180 rpm for 1 day on a rotary shaker. The seed culture thus prepared was used for inoculating 50 ml of a main culture medium, which was composed of 12.0% L-sorbose, 2.0% urea, 0.05% glycerol, 0.25% $MgSO_4.7H_2O$, 3.0% corn steep liquor, 0.4% yeast extract, and 1.5% $CaCO_3$ in a 500 ml Erlenmeyer flask. The cultivation was carried out at 30° C. and 180 rpm for 4 days. The activity assay was performed as described in Example 4. The amount of 2-KGA produced as the enzyme activity was measured at a wavelength of 340 nm by a HPLC system that was composed with a UV detector (TOSOH UV8000; Tosoh), a dualpump (TOSOH CCPE; Tosoh), an integrator (Shimadzu C-R6A; Shimadzu) and a column (YMC-Pack Pro C18, YMC). As shown in Table 2, the production efficiency for 2-KGA of the SNDH-gene disruptants was higher than that of the parent strain GOMTR1. The difference of the conversion rate per mol L-sorbose to 2-KGA was about 3%.

TABLE 2

2-KGA production of *G. oxydans* strains having a disrupted SNDH-gene

| Strain | 2-KGA (g/L) | Residual L-sorbose (g/L) | *Molar yield (mol %) |
|---|---|---|---|
| GOMTR1SN::Km | 96.7 | 15.3 | 99.2 |
| GOMTR1 | 98.8 | 9.8 | 95.5 |

*Molar yield: mol 2-KGA produced/mol L-sorbose consumed.

EXAMPLE 6

Introduction of the Plasmids Carrying the SNDH Gene into the SNDH-gene Disruptant of *G. oxydans* DSM 4025

Figure 5:
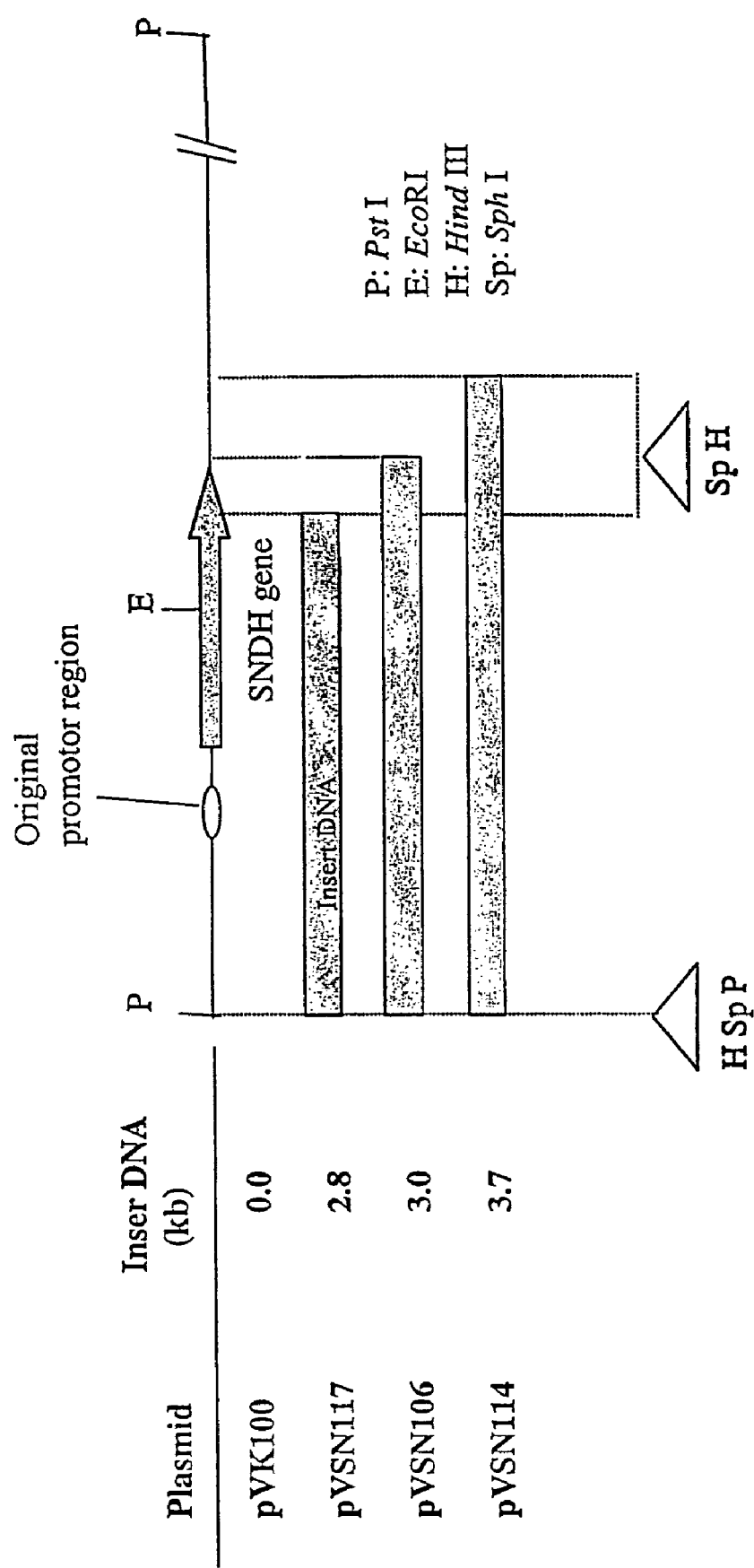
FIG. 5 represents the physical map of the insert DNA of pVSN117, pVSN106, and pVSN114. Plasmid pVSN117 has the insert DNA encoding the C-terminal deleted SNDH gene (nucleotides 258–1955 of SEQ ID NO: 1, i.e., amino acids 1–566 of SEQ ID NO: 2), which expresses only a 55 kba protein. Plasmids pVSN106 and pVSN114 have the insert DNA encoding the intact SNDH gene.

Several kinds of SNDH-expression plasmids using broad host range vector pVK100 were constructed as shown in FIG. 5. Those plasmids have different insert DNAs at the Hind III site of pVK100 described as follows: pVSN117 has the insert DNA containing the incomplete SNDH gene encoding a polypeptide ending at Gly535 of SEQ ID NO: 5 (amino acid residue 566 of SEQ ID NO: 2), i.e., a C-terminal deleted SNDH gene, which expresses only a 55 kDa protein. Plasmids pVSN106 and pVSN114, respectively, have the insert DNA containing the complete SNDH gene. Those plasmids were introduced into strain GOMTR1SN::Km by conjugal transfer method.

The transconjugants having the plasmids shown in FIG. 5 were grown on an agar plate containing 10.0% L-sorbose, 0.25% $MgSO_4.7H_2O$, 1.75% corn steep liquor, 5.0% baker's yeast, 0.5% urea, 0.5% $CaCO_3$, and 2.0% agar at 27° C. for 4 days. The enzyme reaction mixture consisted of 80 μg of cell free extract of the recombinant *Gluconobacter* strains, 25 mM potassium phosphate buffer (pH 7.0), 50 mM of L-sorbosone, and 0.05 mM of PMS. The enzyme reaction was carried out at 30° C. for 30 min with shaking at 1,000 rpm. The activity assay was performed according to Example 4. The result is shown in Table 3.

TABLE 3 production of vitamin C with different SNDH constructs

| Host cell | Vector DNA | Vitamin C produced (mg/L) |
|---|---|---|
| GOMTR1SN::Km-2 | pVK100 | 0.0 |
|  | pVSN117 | 473.2 |
|  | pVSN106 | 845.3 |
|  | pVSN114 | 860.2 |

---

The invention claimed is:

1. An isolated nucleic acid molecule encoding aldehyde dehydrogenase which comprises a polynucleotide being at least 95% identical to the nucleotide sequence of SEQ ID NO: 1.

2. An isolated nucleic acid molecule encoding aldehyde dehydrogenase which comprises a polynucleotide being at least 95% identical to the polynucleotide selected from the group consisting of (a) nucleotides 258–2084 of SEQ ID NO: 1, (b) nucleotides 351–2084 of SEQ ID NO: 1, (c) nucleotides 258–1955 of SEQ ID NO: 1, and (d) nucleotides 351–1955 of SEQ ID NO: 1.

3. An isolated nucleic acid molecule encoding aldehyde dehydrogenase which comprises a polynucleotide selected from the group consisting of (a) a polynucleotide encoding the polypeptide having the amino acid sequence of SEQ ID NO: 2, (b) a polynucleotide encoding the polypeptide consisting of amino acids 32–609 of SEQ ID NO: 2, (c) a polynucleotide encoding the polypeptide consisting of amino acids 1–566 of SEQ ID NO: 2, and (d) a polynucleotide encoding the polypeptide consisting of amino acids 32–566 of SEQ ID NO: 2.

4. An isolated nucleic acid molecule encoding a polypeptide having aldehyde dehydrogenase activity, wherein said nucleic acid molecule hybridizes under stringent conditions to the complementary strand of a nucleic acid molecule of claim 1, wherein the stringent conditions comprise hybridizing overnight at about 42° C. in a hybridization solution comprising 50% formamide, 5×SSC, 0.2% sodium dodecyl sulfate, 0.1% N-lauroylsarcosine, and 2% blocking reagent, followed by washing in a solution comprising 0.1×SSC at about 60° C.

5. An expression vector which comprises the nucleic acid molecule of claim 1.

6. The expression vector of claims 5, wherein said vector is selected from the group consisting of pQE, pUC, pBluescript II, pACYC177, pACYC184, pVK100 and RSF1010.

7. A recombinant microorganism or a plant cell which is transformed with the expression vector of claim 5.

8. A recombinant microorganism or a plant cell which comprises the nucleic acid molecule of claim 1 integrated into its chromosomal DNA.

9. The microorganism of claim 8, wherein said microorganism is selected from the group consisting of bacteria and yeast.

10. The recombinant microorganism of claim 9, wherein said microorganism is selected from the group consisting of

*Gluconobacter, Acetobacter, Pseudomonas, Klebsiella, Acinetobacter,* and *Escherichia*.

11. The recombinant microorganism of claim 10, wherein said microorganism is *Gluconobacter oxydans* DSM 4025.

12. A process for the production of 2-keto-L-gulonic acid (2-KGA) and/or vitamin C from L-sorbosone comprising (a) cultivating the recombinant microorganism of claim 8 in an appropriate culture medium, and (b) recovering and separating 2-KGA and/or vitamin C from said culture medium.

13. A process for the production of 2-KGA from L-sorbosone comprising (a) cultivating a microorganism belonging to *Gluconobacter oxydans* DSM 4025 in an appropriate culture medium, wherein the gene encoding aldehyde dehydrogenase represented by SEQ ID NO: 2 is disrupted in said microorganism, and (b) recovering and separating 2-KGA from said culture medium.

14. A process for the production of aldehyde dehydrogenase comprising (a) cultivating a recombinant microorganism comprising a nucleic acid molecule of claim 1 in an appropriate culture medium, and (b) recovering and separating said aldehyde dehydrogenase from said culture medium.

* * * * *

SEQUENCE LISTING

<160> NUMBER OF SEQ ID NOS: 9

<210> SEQ ID NO 1
<211> LENGTH: 3408
<212> TYPE: DNA
<213> ORGANISM: Gluconobacter oxydans

<400> SEQUENCE: 1

```
gcgactggca gcagcgcaac tatgaccact atggcctgcc gccctattgg atctaactga      60
tccagtaagc caccatcagc cggccctgc ggggccggc ttttgcgct agaccccgcc      120 gaggtgctgt cgtaacctaa ggtcacatct ttacttccac atccgccctt gtcagttctg     180
acgtgacaaa ttgtcgcggt catgctgctg aatgcggatg ccagtcccag atccaagccc     240
gacgcaagga gacgtagatg ttacccaaat cattgaaaca taagaatggc gccatgcgcc     300
ttgtcgcagc ctcgacccctt gcgctgatga tcggcgcggg tgcccatgcg caggtaaacc     360
cggtcgaagt gccggtgggc gcgaacgaga cctttacctc gcgcgtgctg accaccggcc     420
tgtcgaaccc ttgggaaatc acctgggcc ccgacaatat gctgtgggtg accgagcgat     480
cttccggcga agtgacgcgc gtcgacccca ataccggcga gcagcaggtc ctgctgaccc     540
tgaccgattt cagcgtcgat gtgcaacacc agggcctact tggcctcgcg ctgcatcctg     600
agtttatgca agagagcggc aacgactacg tctatatcgt ctacacttat aacaccggca     660
ccgaagaagc gcccgatccg catcaaaagc tggtgcgtta tgcctatgac gctgccgcgc     720
agcagctggt cgatccggtt gatctggtcg caggcattcc cgcaggcaac gaccacaatg     780
gcggtcgcat caaattcgcc cccgatgcc aacacatctt ttacacgctg ggcgagcaag     840
gcgcgaactt tggcggtaac ttccgccgtc cgaaccacgc gcaactgctg ccgacgcaag     900
```

-continued

```
agcaggtcga cgcgggcgat tgggtcgcct attcgggcaa gatcctgcgc gtgaaccttg    960
acggcacgat ccccgaagac aaccccgaga tcgagggcgt gcgtagccat atctttacct   1020
atggccaccg taacccgcag ggcatcacct ttggccccga cggcaccatt tatgccaccg   1080
aacacggccc cgatacggat gacgagctga acatcatcgc cggcggtggc aactatgggt   1140
ggccgaatgt ggccggctat cgcgatggca atcctatgt ctacgctgat tggagccaag    1200
cgcccgctga ccagcgttac accggtcgcg ccggtatccc cgacaccgtg ccgcaattcc   1260
ccgagctgga attcgcgccc gagatggtcg atccgctgac aacctattgg acggtggata   1320
atgattacga tttcaccgcc aattgcggct ggatctgtaa tccgacgatc gcgccttcgt   1380
ctgcctatta ctatgcggcg ggcgagagcg gtatcgcggc ttgggataat tcgatcctga   1440
tcccgacgct gaaacatggc ggcatctatg tgcagcacct cagcgatgat ggccaatctg   1500
tcgacggcct gcccgagctg tggttcagca cccagaaccg ctatcgcgat atcgagatca   1560
gccccgataa ccatgttttt gtggcgaccg acaactttgg cacctcggcg cagaaatatg   1620
gcgagaccgg ctttaccaac gtgctgcata accccggcgc gatccttgtc tttagctatg   1680
tcggcgagga tgctgcgggt cagaccggaa tgatgaccgc gcccgcaccg cagacgcaat   1740
acacgcaagt gcccgccgag ggtgcaggcg cgggcgcgac tgaggttgcg gatgtcgatt   1800
acgacacgct gttcaccgaa ggccagaccc tttatggcag cgcatgtgcc gcgtgccatg   1860
gtgccgctgg ccaaggtgcg cagggcccga cctttgtggg cgtgccggat gtgacgggtg   1920
acaaggacta ccttgcccgc accatcatcc acggttttgg ctatatgccg tcgtttgcga   1980
ctcggctgga tgacgaggag gttgccgcca tcgcgacctt tatccgcaac agctggggca   2040
atgacgaagg catcctgacc ccggccgagg ccgctgccac ccgctgaatg ctgtaaaaac   2100
caccctcgcc tgcacatcag gcgggggtat ttcatttatt ttcacatctg cctttgacat   2160
gtgccgctat cacggttaat gcggcccttc ggctgttctg ggtctaagcg ggtgtgttgc   2220
ccgataagag agacggttca gtccctcccg ccctatttag ggcccattta ggcagaatag   2280
ttttgactca tcaaaatatc gccgcgcctc tggccgcggc cctttcgcaa cgtggatatg   2340
aaacgctgac cgccgtgcag caagctgtgc ttgcgcccga ggctgatggc cgcgacctgc   2400
tggtgtcggc acagaccggt tcgggtaaga cggtggcctt tggtatcgca gtcgcgcccg   2460
acctttgggg cgacgacaat atcctgccgc tgaacacgcc gcctgttgcg ctgttcatcg   2520
cccccacgcg cgagcttgcg ctgcaagttg ctcaggaact gacctggctt tacgccaatg   2580
caggtgccca gatcgcgacc tgcgtcggcg gtatggatta ccgcaccgag cgccgcgccc   2640
ttgcacgtct gccgcaaatc gttgtcggca cgcccggccg tctgcgcgac catatcgacc   2700
gtggcggcct tgacctgtcc gaattgcgcg tgaccgtgct ggacgaagcg gatgagatgc   2760
tcgacctcgg cttccgcgat gatctgcaat atatcttgca agccgcgccc gaagatcgcc   2820
gcacgctgat gttctcggcc accgtgccgc gcgagattga aaaactggcc cgcgacttcc   2880
aaaatgacgc cctgcgtctg gaaacccgtg gcgaggccaa gcagcacaac gacatcagct   2940
accaagcttt gtcggtcacc atgcgcgatc gcgaaaacgc cattttcaac atgctgcgtt   3000
tttatgaatc gcgcacggcg atcatcttct gcaagacccg cgccaatgtg aatgatctgc   3060
tgtcgcggat gagcggtcgt ggcttccgcg tggtggccct gtcgggcgag ctgtcgcaac   3120
aggaacgcac caacgcgctg caagcgctgc gtgatggccg cgccaacgtt tgtatcgcga   3180
ccgacgtcgc ggcgcgcggc attgacttgc cgggcctcga gctggtgatc cactacgatc   3240
tgccgaccaa tgccgaaacc ctgctgcacc gctcgggccg taccggccgc cgggtgccaa   3300
```

```
gggcgtctcg gcgctgatcg tcacccccgg cgatttcaaa aaagcgcagc gtttgctgag    3360
ctttgccaaa gtgaccgcgg aatggggcaa ggcgccttcg ccgaaga                 3408
```

<210> SEQ ID NO 2
<211> LENGTH: 609
<212> TYPE: PRT
<213> ORGANISM: Gluconobacter oxydans

<400> SEQUENCE: 2

```
Met Leu Pro Lys Ser Leu Lys His Lys Asn Gly Ala Met Arg Leu Val
 1               5                  10                  15

Ala Ala Ser Thr Leu Ala Leu Met Ile Gly Ala Gly Ala His Ala Gln
            20                  25                  30

Val Asn Pro Val Glu Val Pro Gly Ala Asn Glu Thr Phe Thr Ser
        35                  40                  45

Arg Val Leu Thr Thr Gly Leu Ser Asn Pro Trp Glu Ile Thr Trp Gly
50                  55                  60

Pro Asp Asn Met Leu Trp Val Thr Glu Arg Ser Ser Gly Glu Val Thr
65                  70                  75                  80

Arg Val Asp Pro Asn Thr Gly Glu Gln Gln Val Leu Leu Thr Leu Thr
                85                  90                  95

Asp Phe Ser Val Asp Val Gln His Gln Gly Leu Leu Gly Leu Ala Leu
            100                 105                 110

His Pro Glu Phe Met Gln Glu Ser Gly Asn Asp Tyr Val Tyr Ile Val
        115                 120                 125

Tyr Thr Tyr Asn Thr Gly Thr Glu Glu Ala Pro Asp Pro His Gln Lys
130                 135                 140

Leu Val Arg Tyr Ala Tyr Asp Ala Ala Gln Gln Leu Val Asp Pro
145                 150                 155                 160

Val Asp Leu Val Ala Gly Ile Pro Ala Gly Asn Asp His Asn Gly Gly
                165                 170                 175

Arg Ile Lys Phe Ala Pro Asp Gly Gln His Ile Phe Tyr Thr Leu Gly
            180                 185                 190

Glu Gln Gly Ala Asn Phe Gly Gly Asn Phe Arg Arg Pro Asn His Ala
        195                 200                 205

Gln Leu Leu Pro Thr Gln Glu Gln Val Asp Ala Gly Asp Trp Val Ala
210                 215                 220

Tyr Ser Gly Lys Ile Leu Arg Val Asn Leu Asp Gly Thr Ile Pro Glu
225                 230                 235                 240

Asp Asn Pro Glu Ile Glu Gly Val Arg Ser His Ile Phe Thr Tyr Gly
                245                 250                 255

His Arg Asn Pro Gln Gly Ile Thr Phe Gly Pro Asp Gly Thr Ile Tyr
            260                 265                 270

Ala Thr Glu His Gly Pro Asp Thr Asp Glu Leu Asn Ile Ile Ala
        275                 280                 285

Gly Gly Gly Asn Tyr Gly Trp Pro Asn Val Ala Gly Tyr Arg Asp Gly
290                 295                 300

Lys Ser Tyr Val Tyr Ala Asp Trp Ser Gln Ala Pro Ala Asp Gln Arg
305                 310                 315                 320

Tyr Thr Gly Arg Ala Gly Ile Pro Asp Thr Val Pro Gln Phe Pro Glu
                325                 330                 335

Leu Glu Phe Ala Pro Glu Met Val Asp Pro Leu Thr Thr Tyr Trp Thr
            340                 345                 350
```

```
Val Asp Asn Asp Tyr Asp Phe Thr Ala Asn Cys Gly Trp Ile Cys Asn
            355                 360                 365

Pro Thr Ile Ala Pro Ser Ser Ala Tyr Tyr Ala Ala Gly Glu Ser
    370                 375                 380

Gly Ile Ala Ala Trp Asp Asn Ser Ile Leu Ile Pro Thr Leu Lys His
385                 390                 395                 400

Gly Gly Ile Tyr Val Gln His Leu Ser Asp Asp Gly Gln Ser Val Asp
                405                 410                 415

Gly Leu Pro Glu Leu Trp Phe Ser Thr Gln Asn Arg Tyr Arg Asp Ile
                420                 425                 430

Glu Ile Ser Pro Asp Asn His Val Phe Val Ala Thr Asp Asn Phe Gly
            435                 440                 445

Thr Ser Ala Gln Lys Tyr Gly Glu Thr Gly Phe Thr Asn Val Leu His
    450                 455                 460

Asn Pro Gly Ala Ile Leu Val Phe Ser Tyr Val Gly Glu Asp Ala Ala
465                 470                 475                 480

Gly Gln Thr Gly Met Met Thr Ala Pro Ala Pro Gln Thr Gln Tyr Thr
                485                 490                 495

Gln Val Pro Ala Glu Gly Ala Gly Ala Gly Ala Thr Glu Val Ala Asp
                500                 505                 510

Val Asp Tyr Asp Thr Leu Phe Thr Glu Gly Gln Thr Leu Tyr Gly Ser
            515                 520                 525

Ala Cys Ala Ala Cys His Gly Ala Ala Gly Gln Gly Ala Gln Gly Pro
    530                 535                 540

Thr Phe Val Gly Val Pro Asp Val Thr Gly Asp Lys Asp Tyr Leu Ala
545                 550                 555                 560

Arg Thr Ile Ile His Gly Phe Gly Tyr Met Pro Ser Phe Ala Thr Arg
                565                 570                 575

Leu Asp Asp Glu Glu Val Ala Ala Ile Ala Thr Phe Ile Arg Asn Ser
            580                 585                 590

Trp Gly Asn Asp Glu Gly Ile Leu Thr Pro Ala Glu Ala Ala Ala Thr
    595                 600                 605

Arg
```

<210> SEQ ID NO 3
<211> LENGTH: 14
<212> TYPE: PRT
<213> ORGANISM: Gluconobacter oxydans
<220> FEATURE:
<221> NAME/KEY: X
<222> LOCATION: (2)..(2)
<223> OTHER INFORMATION: X can be any naturally occuring amino acid.
<220> FEATURE:
<221> NAME/KEY: X
<222> LOCATION: (4)..(4)
<223> OTHER INFORMATION: X is P or K.

<400> SEQUENCE: 3

```
Gln Xaa Asn Xaa Val Glu Val Pro Val Gly Ala Asn Glu Thr
1               5                   10
```

<210> SEQ ID NO 4
<211> LENGTH: 31
<212> TYPE: PRT
<213> ORGANISM: Gluconobacter oxydans

<400> SEQUENCE: 4

```
Met Leu Pro Lys Ser Leu Lys His Lys Asn Gly Ala Met Arg Leu Val
1               5                   10                  15
```

```
Ala Ala Ser Thr Leu Ala Leu Met Ile Gly Ala Gly Ala His Ala
            20                  25                  30
```

<210> SEQ ID NO 5
<211> LENGTH: 578
<212> TYPE: PRT
<213> ORGANISM: Gluconobacter oxydans

<400> SEQUENCE: 5

```
Gln Val Asn Pro Val Glu Val Pro Val Gly Ala Asn Glu Thr Phe Thr
1               5                   10                  15

Ser Arg Val Leu Thr Thr Gly Leu Ser Asn Pro Trp Glu Ile Thr Trp
            20                  25                  30

Gly Pro Asp Asn Met Leu Trp Val Thr Glu Arg Ser Ser Gly Glu Val
        35                  40                  45

Thr Arg Val Asp Pro Asn Thr Gly Glu Gln Gln Val Leu Leu Thr Leu
    50                  55                  60

Thr Asp Phe Ser Val Asp Val Gln His Gln Gly Leu Leu Gly Leu Ala
65                  70                  75                  80

Leu His Pro Glu Phe Met Gln Ser Gly Asn Asp Tyr Val Tyr Ile
                85                  90                  95

Val Tyr Thr Tyr Asn Thr Gly Thr Glu Glu Ala Pro Asp Pro His Gln
            100                 105                 110

Lys Leu Val Arg Tyr Ala Tyr Asp Ala Ala Gln Gln Leu Val Asp
        115                 120                 125

Pro Val Asp Leu Val Ala Gly Ile Pro Ala Gly Asn Asp His Asn Gly
    130                 135                 140

Gly Arg Ile Lys Phe Ala Pro Asp Gly Gln His Ile Phe Tyr Thr Leu
145                 150                 155                 160

Gly Glu Gln Gly Ala Asn Phe Gly Gly Asn Phe Arg Arg Pro Asn His
                165                 170                 175

Ala Gln Leu Leu Pro Thr Gln Glu Gln Val Asp Ala Gly Asp Trp Val
            180                 185                 190

Ala Tyr Ser Gly Lys Ile Leu Arg Val Asn Leu Asp Gly Thr Ile Pro
        195                 200                 205

Glu Asp Asn Pro Glu Ile Glu Gly Val Arg Ser His Ile Phe Thr Tyr
    210                 215                 220

Gly His Arg Asn Pro Gln Gly Ile Thr Phe Gly Pro Asp Gly Thr Ile
225                 230                 235                 240

Tyr Ala Thr Glu His Gly Pro Asp Thr Asp Glu Leu Asn Ile Ile
                245                 250                 255

Ala Gly Gly Gly Asn Tyr Gly Trp Pro Asn Val Ala Gly Tyr Arg Asp
            260                 265                 270

Gly Lys Ser Tyr Val Tyr Ala Asp Trp Ser Gln Ala Pro Ala Asp Gln
        275                 280                 285

Arg Tyr Thr Gly Arg Ala Gly Ile Pro Asp Thr Val Pro Gln Phe Pro
    290                 295                 300

Glu Leu Glu Phe Ala Pro Glu Met Val Asp Pro Leu Thr Thr Tyr Trp
305                 310                 315                 320

Thr Val Asp Asn Asp Tyr Asp Phe Thr Ala Asn Cys Gly Trp Ile Cys
                325                 330                 335

Asn Pro Thr Ile Ala Pro Ser Ser Ala Tyr Tyr Ala Ala Gly Glu
            340                 345                 350

Ser Gly Ile Ala Ala Trp Asp Asn Ser Ile Leu Ile Pro Thr Leu Lys
```

-continued

```
                    355                 360                 365
His Gly Gly Ile Tyr Val Gln His Leu Ser Asp Asp Gly Gln Ser Val
            370                 375                 380

Asp Gly Leu Pro Glu Leu Trp Phe Ser Thr Gln Asn Arg Tyr Arg Asp
385                 390                 395                 400

Ile Glu Ile Ser Pro Asp Asn His Val Phe Val Ala Thr Asp Asn Phe
                405                 410                 415

Gly Thr Ser Ala Gln Lys Tyr Gly Glu Thr Gly Phe Thr Asn Val Leu
            420                 425                 430

His Asn Pro Gly Ala Ile Leu Val Phe Ser Tyr Val Gly Glu Asp Ala
                435                 440                 445

Ala Gly Gln Thr Gly Met Met Thr Ala Pro Ala Pro Gln Thr Gln Tyr
            450                 455                 460

Thr Gln Val Pro Ala Glu Gly Ala Gly Ala Thr Glu Val Ala
465                 470                 475                 480

Asp Val Asp Tyr Asp Thr Leu Phe Thr Glu Gly Gln Thr Leu Tyr Gly
                485                 490                 495

Ser Ala Cys Ala Ala Cys His Gly Ala Ala Gly Gln Gly Ala Gln Gly
            500                 505                 510

Pro Thr Phe Val Gly Val Pro Asp Val Thr Gly Asp Lys Asp Tyr Leu
                515                 520                 525

Ala Arg Thr Ile Ile His Gly Phe Gly Tyr Met Pro Ser Phe Ala Thr
            530                 535                 540

Arg Leu Asp Asp Glu Glu Val Ala Ala Ile Ala Thr Phe Ile Arg Asn
545                 550                 555                 560

Ser Trp Gly Asn Asp Glu Gly Ile Leu Thr Pro Ala Glu Ala Ala
                565                 570                 575

Thr Arg
```

```
<210> SEQ ID NO 6
<211> LENGTH: 17
<212> TYPE: DNA
<213> ORGANISM: Artificial
<220> FEATURE:
<223> OTHER INFORMATION: an artificially synthesized primer sequence
<220> FEATURE:
<221> NAME/KEY: r
<222> LOCATION: (3)..(3)
<223> OTHER INFORMATION: r is g or a
<220> FEATURE:
<221> NAME/KEY: y
<222> LOCATION: (6)..(6)
<223> OTHER INFORMATION: y is t/u or c
<220> FEATURE:
<221> NAME/KEY: s
<222> LOCATION: (12)..(12)
<223> OTHER INFORMATION: s is g or c
<220> FEATURE:
<221> NAME/KEY: b
<222> LOCATION: (15)..(15)
<223> OTHER INFORMATION: b is g or c or t/u

<400> SEQUENCE: 6
carggyaacc csgtbga                                                 17

<210> SEQ ID NO 7
<211> LENGTH: 17
<212> TYPE: DNA
<213> ORGANISM: Artificial
<220> FEATURE:
<223> OTHER INFORMATION: an artificially synthesized primer sequence
<220> FEATURE:
```

```
<221> NAME/KEY: y
<222> LOCATION: (3)..(3)
<223> OTHER INFORMATION: y is t/u or c
<220> FEATURE:
<221> NAME/KEY: n
<222> LOCATION: (9)..(9)
<223> OTHER INFORMATION: n is a or g or c or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: r
<222> LOCATION: (12)..(12)
<223> OTHER INFORMATION: r is g or a
<220> FEATURE:
<221> NAME/KEY: v
<222> LOCATION: (15)..(15)
<223> OTHER INFORMATION: v is a or g or c

<400> SEQUENCE: 7
gtytcgttng crccvac                                              17

<210> SEQ ID NO 8
<211> LENGTH: 15
<212> TYPE: DNA
<213> ORGANISM: Artificial
<220> FEATURE:
<223> OTHER INFORMATION: an artificially synthesized primer sequence

<400> SEQUENCE: 8
cagggtaacc cggtc                                                15

<210> SEQ ID NO 9
<211> LENGTH: 15
<212> TYPE: DNA
<213> ORGANISM: Artificial
<220> FEATURE:
<223> OTHER INFORMATION: an artificially synthesized primer sequence

<400> SEQUENCE: 9
gactcgtttg cgccc                                                15
```